United States Patent
Goodwin

(10) Patent No.: US 6,413,265 B1
(45) Date of Patent: Jul. 2, 2002

(54) SCALPEL

(76) Inventor: J. C. Goodwin, 1316 W. Gurley St., Prescott, AZ (US) 86305

( * ) Notice: Subject to any disclaimer, the term of this patent is extended or adjusted under 35 U.S.C. 154(b) by 0 days.

(21) Appl. No.: 09/515,237

(22) Filed: Mar. 6, 2000

(51) Int. Cl.[7] ............................................. A61B 17/32
(52) U.S. Cl. ................................................... 606/167
(58) Field of Search ........................ 606/1, 166, 167; 30/1, 32, 48, 49; 433/144, 46, 229

(56) References Cited

U.S. PATENT DOCUMENTS

| | | | | |
|---|---|---|---|---|
| 1,455,374 A | * | 5/1923 | Ziesel | 433/144 |
| 3,411,211 A | * | 11/1968 | Fountain | 433/144 |
| 3,471,929 A | * | 10/1969 | Boone | 433/144 |
| 4,270,902 A | * | 6/1981 | Wiland | 433/144 |
| 4,672,964 A | * | 6/1987 | Dee et al. | 606/167 |
| 5,055,106 A | * | 10/1991 | Lundgren | 606/167 |
| 5,423,841 A | * | 6/1995 | Kornefeld | 606/167 |

* cited by examiner

*Primary Examiner*—Kevin Shaver
*Assistant Examiner*—Brian Szmal
(74) *Attorney, Agent, or Firm*—Cahill, Sutton & Thomas P.L.C.

(57) ABSTRACT

A scalpel particularly useful in dental restoration has a flattened handle of ovoidal shape having a cusp blade mounted at one end thereof. The blade is preferably positioned on the handle so that it extends away from the handle at acute angles to an imaginary horizontal plane, an imaginary longitudinal vertical plane and an imaginary transverse vertical plane.

25 Claims, 3 Drawing Sheets

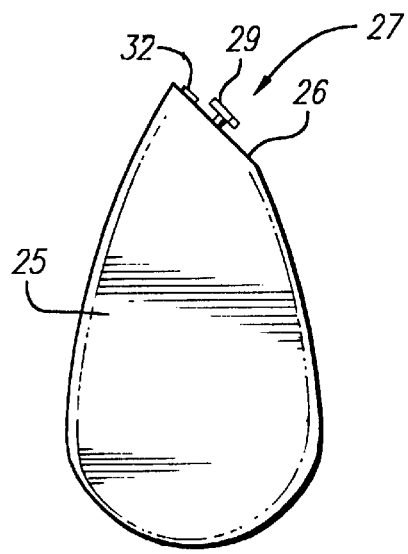
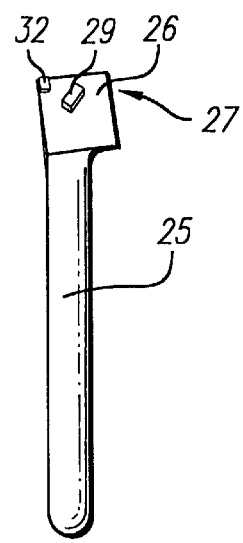
FIG. 8          FIG. 9
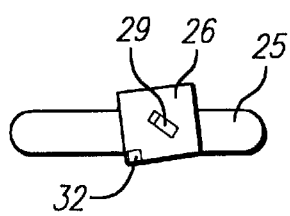
FIG. 10
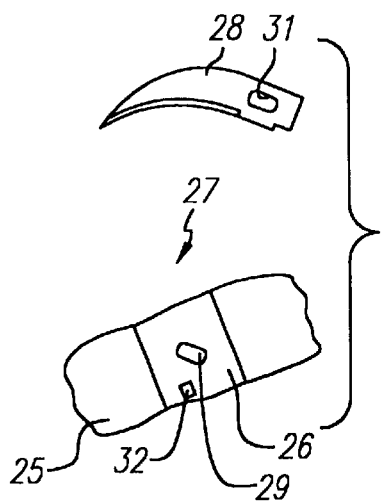
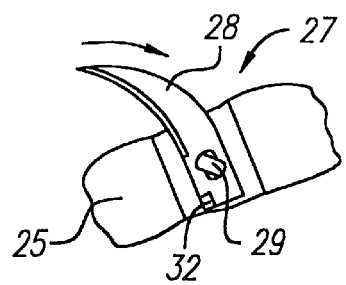
FIG. 11
FIG. 12

SCALPEL

TECHNICAL FIELD

This invention is concerned with improving the performance of scalpels particularly useful in dental restorations.

BACKGROUND ART

Medical scalpels designed for soft tissue surgery typically have thin, elongated handles adapted to hold a blade extending axially from the handle.

In composite resin restoration of teeth there are often small ledges or overhangs present at the edges of the restorations. This excess material must be removed from the surface of the tooth and from between adjoining teeth to provide a smooth, hygienic surface.

The typical surgical scalpel with a 5" to 6" handle and straight or angled blade can be used to remove excess material from the front (anterior) teeth. However, anatomic considerations and limited accessibility prevent such an instrument from being used to remove the excess material from the bicuspid or molar teeth in the posterior segment of the mouth.

SUMMARY OF THE INVENTION

This invention provides a flat, fairly wide handle to be gripped between the distal phalanx regions of the thumb and the index finger. The shape of the handle can be ovoidal of a size to comfortably cover the distal phalanx region of the thumb. The handle carries a short cusp blade positioned at acute angles to an imaginary horizontal plane through the handle and imaginary vertical longitudinal and transverse planes through the handle. The scalpels are preferably used in pairs with one having a right angled blade and the other a left angled blade. As such, the pair enable the dentist to work with both the facial and lingual aspects of the teeth.

BRIEF DESCRIPTION OF THE DRAWINGS

The invention is described in greater detail hereafter by reference to the accompanying drawings wherein:

FIG. 8 is a plan view of a modified handle for manipulating a removable blade;

FIG. 9 is a side elevational view of the handle of FIG. 8;

FIG. 10 is a front elevational view of the handle of FIG. 8;

FIG. 11 is an exploded fragmentary view illustrating the assembly of a blade to the handle of FIG. 8; and FIG. 12 is a fragmentary view of the handle and blade combination.

BEST MODE FOR CARRYING OUT THE INVENTION

Figure 1:
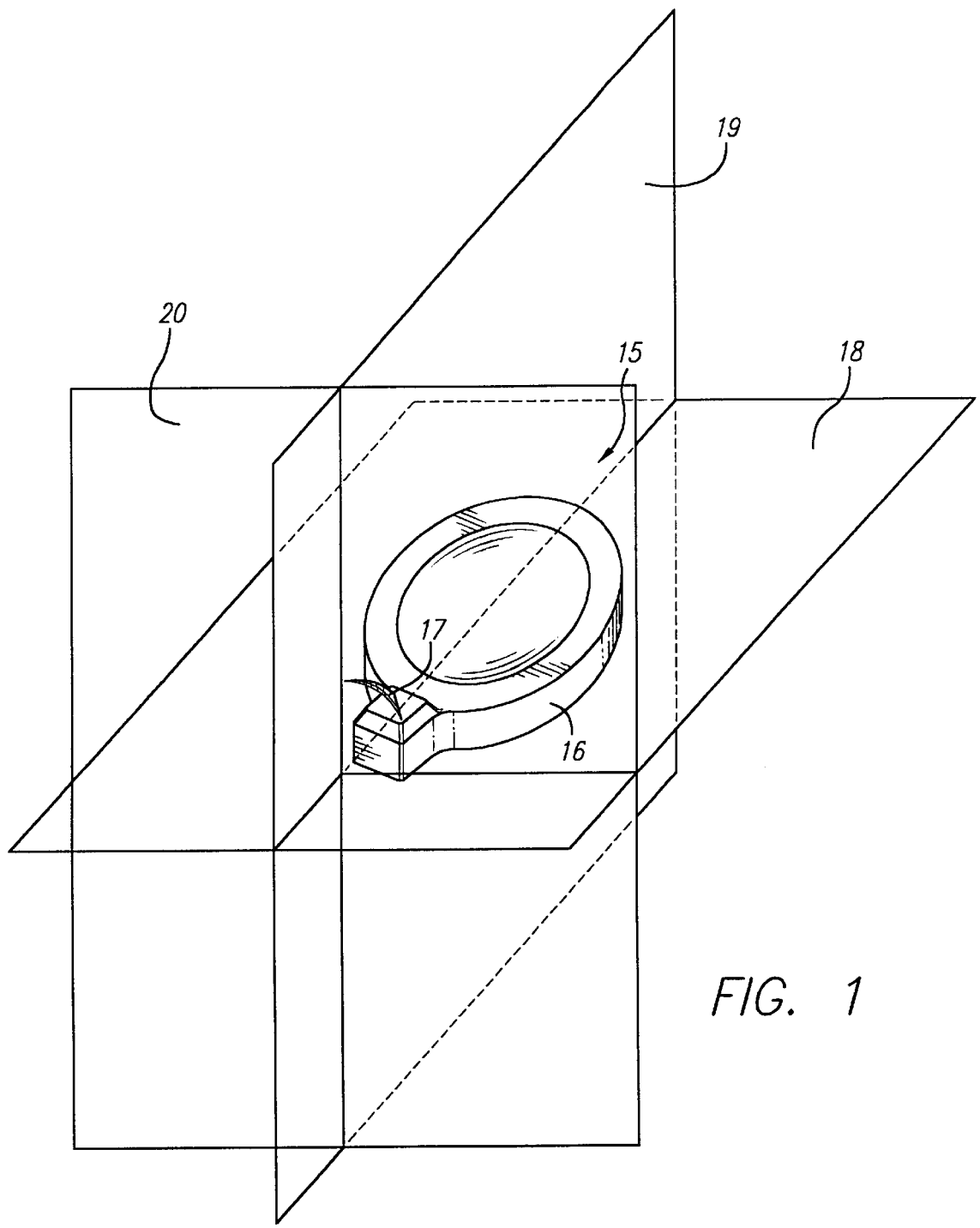
FIG. 1 is a perspective view of a scalpel constructed in accordance with this invention with three planes of reference imposed therein.
Figure 2:
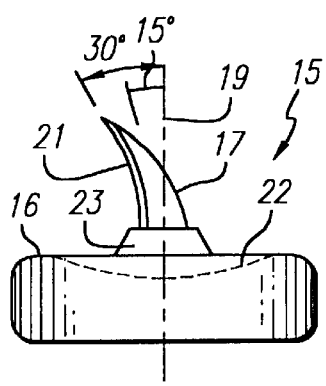
FIG. 2 is a rear elevational view of the scalpel.
Figure 3:
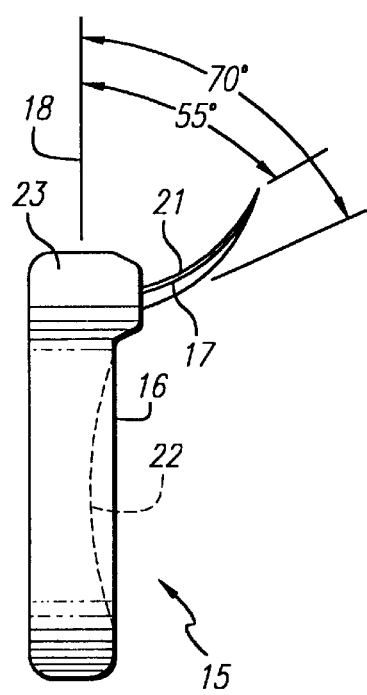
FIG. 3 is a side elevational view of the scalpel.
Figure 4:
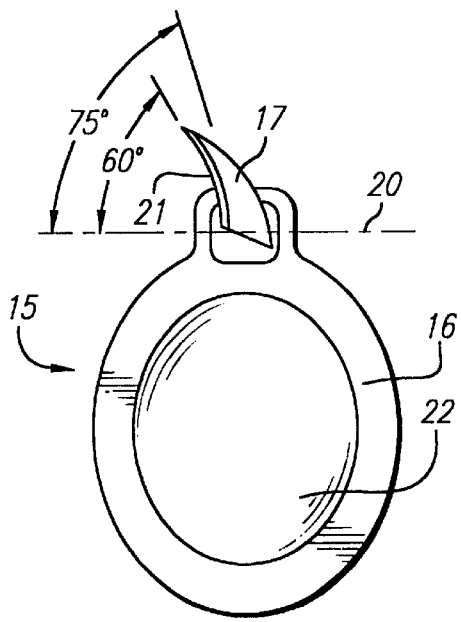
FIG. 4 is a plan view of the scalpel.
Figure 5:
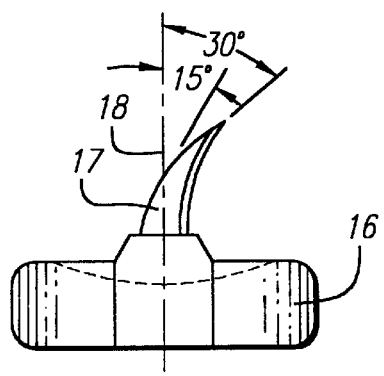
FIG. 5 is a rear elevational view of a companion scalpel.
Figure 6:
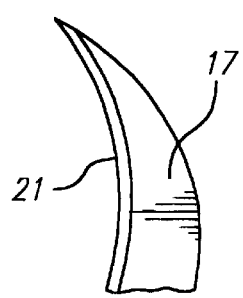
FIG. 6 is an enlarged fragmentary view of the face of a blade for the scalpel.
Figure 7:
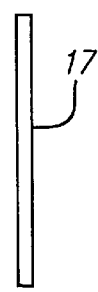
FIG. 7 is an edge view of the blade of FIG. 6.

Referring first to FIGS. 1 through 7, there is illustrated a scalpel, indicated generally by reference numeral 15, which is comprised of a handle 16 and a blade 17.

Superimposed on the scalpel 15 illustrated in FIG. 1 are three imaginary reference planes by which the positioning of the blade 17 in reference to the handle 16 is ascertained. A horizontal plane 18 conforms to the flat, wide body of the handle 16. A vertical plane 19 passes longitudinally through the handle 16. The third plane 20 is a vertical plane passing transversely through the handle 16. In accordance with this invention the blade 17 is disposed at an acute angle with respect to the horizontal plane 18 and preferably at an acute angle also with respect to one or both of planes 19 and 20.

Empirical evidence suggests that the blade 17 preferably is positioned at an angle with respect to the horizontal plane 18 of between approximately 55° and approximately 70° (See FIG. 3) This same evidence suggests that the blade 17 preferably is positioned at an angle with respect to the longitudinal vertical plane 19 of between approximately 15° and approximately 30°. (See FIG. 2) And this same evidence suggests that the blade 17 preferably is positioned at an angle with respect to the transverse vertical plane 20 of between approximately 60° and approximately 75°. (See FIG. 4)

It has further been determined from empirical studies that a blade 17 with a cusp configuration and having a sharpened concave edge 21 is preferred. (See FIGS. 6 and 7) The blade 17 can be made from stainless steel or carbon steel.

The scalpel 15 illustrated in FIGS. 1 through 5 is intended to be disposable, i.e., used on one patient and discarded. To this end the handle 16, in which the blade 17 is permanently embedded, is preferably formed from an inexpensive material, such as plastic, that can be cast or molded.

The precise shape of the handle 16 is not critical to the invention although the flattened ovoidal or pyriform, or pear-shaped, configuration in which the handle has a greater width than thickness is preferred. The transverse and longitudinal dimensions of the handle 16 are such as to comfortably be grasped between the phalanx regions of the thumb and the index finger so the scalpel can be manipulated with a hand twisting motion. The handle 16 may be serrated or provided with a recess, or indentation, 22 in its upper or lower or both surfaces. The handle 16 also preferably has a thickened front, or nose, region 23 for securely retaining the blade 17 in the handle.

It is also contemplated that the invention can be utilized in scalpels having a reusable handle to which blades can be attached and removed. One such scalpel is illustrated in FIGS. 8 through 12. The handle for this scalpel, identified by reference numeral 25, is preferably formed from cast or machined metal into the flattened, pear-shaped configuration. The nose 26 of handle 25 is provided with an attachment mechanism 27 by which a blade 28 can be secured to and removed from the handle. This mechanism 27 may take the form of a stud 29 protruding from the nose 26 of the handle and having a non-circular head at its distal end. The blade 28 is provided with a cooperating opening 31 sized to slip over the head of stud 29 (See FIG. 11). The blade 28 is then rotated on the stud 29 as shown in FIG. 12 to engage a stop 32 to become locked beneath the head of the stud 29.

If desired, of course, a different attachment mechanism, such as a screw or screws, can be employed to secure the blade 28 onto handle 25.

The nose 26 of handle 25 is angled with respect to the imaginary reference planes mentioned above so as to cause the blade 28 to project within the angle ranges also mentioned above.

What is claimed is:

1. A scalpel having a handle adapted to be grasped between the distal phalanx region of the thumb and the index finger, said handle possessing a flattened shape with greater width than thickness and sized to comfortably cover the distal phalanx region of the thumb, and a blade protruding upwardly from one end of the handle in relation to an imaginary horizontal plane containing the handle.

2. The scalpel of claim 1 wherein said blade extends at an acute angle with respect to the horizontal plane.

3. The scalpel of claim 1 wherein said blade extends at an acute angle with respect to an imaginary vertical plane passing longitudinally through the handle.

4. The scalpel of claim 2 wherein said blade extends at an acute angle with respect to an imaginary vertical plane passing longitudinally through the handle.

5. The scalpel of claim 1 wherein said blade extends at an acute angle with respect to an imaginary vertical plane passing transversely through the handle.

6. The scalpel of claim 2 wherein said blade extends at an acute angle with respect to an imaginary vertical plane passing transversely through the handle.

7. The scalpel of claim 3 wherein said blade extends at an acute angle with respect to an imaginary vertical plane passing transversely through the handle.

8. The scalpel of claim 4 wherein said blade extends at an acute angle with respect to an imaginary vertical plane passing transversely through the handle.

9. The scalpel of claim 1 wherein said blade has a cusp shape with a sharpened concave edge.

10. The scalpel of claim 2 wherein said blade has a cusp shape with a sharpened concave edge.

11. The scalpel of claim 3 wherein said blade has a cusp shape with a sharpened concave edge.

12. The scalpel of claim 4 wherein said blade has a cusp shape with a sharpened concave edge.

13. The scalpel of claim 5 wherein said blade has a cusp shape with a sharpened concave edge.

14. The scalpel of claim 6 wherein said blade has a cusp shape with a sharpened concave edge.

15. The scalpel of claim 7 wherein said blade has a cusp shape with a sharpened concave edge.

16. The scalpel of claim 8 wherein said blade has a cusp shape with a sharpened concave edge.

17. The scalpel of claim 2 wherein the acute angle with respect to the horizontal plane is between approximately 55° and approximately 70°.

18. The scalpel of claim 3 wherein the acute angle with respect to the longitudinal vertical plane is between approximately 15° and approximately 30°.

19. The scalpel of claim 4 wherein the acute angle with respect to the longitudinal vertical plane is between approximately 15° and approximately 30°.

20. The scalpel of claim 5 wherein the acute angle with respect to the transverse vertical plane is between approximately 60° and approximately 75°.

21. The scalpel of claim 6 wherein the acute angle with respect to the transverse vertical plane is between approximately 60° and approximately 75°.

22. The scalpel of claim 7 wherein the acute angle with respect to the transverse vertical plane is between approximately 60° and approximately 57°.

23. The scalpel of claim 8 wherein the acute angle with respect to the transverse vertical plane is between approximately 60° and approximately 75°.

24. The scalpel of claim 1 wherein said handle has an ovoidal shape.

25. A pair of scalpels as recited in claim 4 wherein the angle the blade extends with respect to the vertical longitudinal plane on one scalpel is opposite the same angle on the other scalpel.

* * * * *